(12) United States Patent
Lauenstein (10) Patent No.: US 12,317,925 B2
(45) Date of Patent: Jun. 3, 2025

(54) HEATER ASSEMBLY WITH A PLURALITY OF RECESSES

(71) Applicant: Philip Morris Products S.A., Neuchatel (CH)

(72) Inventor: Stefan Lauenstein, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 1085 days.

(21) Appl. No.: 17/049,210

(22) PCT Filed: Apr. 30, 2019

(86) PCT No.: PCT/EP2019/061123
§ 371 (c)(1),
(2) Date: Oct. 20, 2020

(87) PCT Pub. No.: WO2019/211311
PCT Pub. Date: Nov. 7, 2019

(65) Prior Publication Data
US 2021/0235760 A1 Aug. 5, 2021

(30) Foreign Application Priority Data
Apr. 30, 2018 (EP) .................................... 18170187

(51) Int. Cl.
*A24F 40/40* (2020.01)
*A24F 40/10* (2020.01)
(Continued)

(52) U.S. Cl.
CPC .............. *A24F 40/40* (2020.01); *A24F 40/42* (2020.01); *A24F 40/46* (2020.01); *A24F 40/485* (2020.01); *A24F 40/10* (2020.01)

(58) Field of Classification Search
CPC ........... A24F 40/46; A24F 40/42; A24F 40/40
See application file for complete search history.

(56) References Cited

U.S. PATENT DOCUMENTS 9,609,894 B2 4/2017 Abramov et al.
2011/0155153 A1 6/2011 Thorens et al.
(Continued)

FOREIGN PATENT DOCUMENTS

CA 2 244 210 C 4/2006
CN 102753047 A 10/2012
(Continued)

OTHER PUBLICATIONS

"Corresponding." Merriam-Webster.com Dictionary, Merriam-Webster, https://www.merriam-webster.com/dictionary/corresponding. Accessed Apr. 25, 2024. (Year: 2024).*
(Continued)

*Primary Examiner* — Michael H. Wilson
*Assistant Examiner* — Stephanie Lynn Moore
(74) *Attorney, Agent, or Firm* — Oblon, McClelland, Maier & Neustadt, L.L.P.

(57) ABSTRACT

A heater assembly is provided for an aerosol-generating system having a liquid storage portion configured to hold a liquid aerosol-forming substrate, the heater assembly including: an electric heater configured to heat the substrate to form an aerosol; and a capillary body configured to convey the substrate from the liquid storage portion of the system to the heater, the heater being disposed on an outer surface of the capillary body and including a heating layer including a porous sheet of electrically conductive material, the porous sheet being embossed to define a plurality of recesses on its lower surface configured to retain the substrate by capillary action and a plurality of corresponding raised portions on its upper surface, and at least part of each of the plurality of recesses being spaced from the outer surface of the capillary body in a perpendicular direction.

15 Claims, 3 Drawing Sheets

(51) Int. Cl.
　　　*A24F 40/42* 　　　(2020.01)
　　　*A24F 40/46* 　　　(2020.01)
　　　*A24F 40/485* 　　 (2020.01)

(56) References Cited

U.S. PATENT DOCUMENTS

| | | | |
|---|---|---|---|
| 2013/0081623 A1* | 4/2013 | Buchberger | A61M 11/042 |
| | | | 128/203.27 |
| 2014/0202476 A1* | 7/2014 | Egoyants | H05B 1/0291 |
| | | | 131/329 |
| 2014/0238423 A1 | 8/2014 | Tucker et al. | |
| 2015/0090280 A1 | 4/2015 | Chen | |
| 2015/0264979 A1 | 9/2015 | Thorens et al. | |
| 2017/0027225 A1 | 2/2017 | Buchberger et al. | |
| 2018/0279685 A1 | 10/2018 | Thorens et al. | |
| 2019/0124993 A1 | 5/2019 | Matsumoto et al. | |

FOREIGN PATENT DOCUMENTS

| | | |
|---|---|---|
| CN | 103960782 A | 8/2014 |
| CN | 104522891 A | 4/2015 |
| CN | 104824853 A | 8/2015 |
| CN | 105433446 A | 3/2016 |
| CN | 105919164 A | 9/2016 |
| CN | 205648932 U | 10/2016 |
| CN | 205865985 U | 1/2017 |
| CN | 205962844 U | 2/2017 |
| EA | 000244 B1 | 2/1999 |
| EA | 026473 B1 | 4/2017 |
| EP | 3 136 893 A1 | 3/2017 |
| EP | 3 166 430 A1 | 5/2017 |
| EP | 3 287 017 A1 | 2/2018 |
| JP | 2017-506502 A | 3/2017 |
| JP | 2017-506509 A | 3/2017 |
| JP | 2018-46847 A | 3/2018 |
| KR | 10-2014-0068807 A | 6/2014 |
| KR | 10-2016-105494 A | 9/2016 |
| RU | 2 636 649 C1 | 11/2017 |
| RU | 2 649 822 C2 | 4/2018 |
| WO | WO 2015/043132 A1 | 4/2015 |
| WO | WO 2016/169115 A1 | 10/2016 |
| WO | WO 2017-025310 A1 | 2/2017 |
| WO | WO 2017/207419 A1 | 12/2017 |
| WO | WO 2018/002994 A1 | 1/2018 |

OTHER PUBLICATIONS

Japanese Notice of Allowance issued Mar. 13, 2023 in Japanese Patent Application No. 2020-560931(with English Translation), 4 pages.

Russian Office Action and Search Report issued on Aug. 4, 2022 in Russian Patent Application No. 2020136435 (with English translation), 18 pages.

Combined Chinese Office Action and Search Report issued Aug. 18, 2023 in Chinese Patent Application No. 201980025971.2 (with English Translation), 9 pages.

International Search Report and Written Opinion issued Jul. 19, 2019 in PCT/EP2019/061123 filed Apr. 30, 2019.

Korean Notice of Allowance issued Mar. 18, 2024 in Korean Patent Application No. 10-2020-7030738 (with English Translation), 4 pages.

* cited by examiner

HEATER ASSEMBLY WITH A PLURALITY OF RECESSES

The present invention relates to heater assemblies for aerosol-generating systems, the heater assemblies comprising an electric heater that is suitable for vaporising an aerosol-forming substrate. In particular, the invention relates to handheld aerosol-generating systems, such as electrically operated smoking systems. Aspects of the invention relate to heater assemblies for an aerosol-generating system, cartridges for an aerosol-generating system and to aerosol-generating systems incorporating such heater assemblies.

One type of aerosol-generating system is an electrically operated smoking system. Handheld electrically operated smoking systems consisting of a device portion comprising a battery and control electronics, and a cartridge portion comprising a supply of aerosol-forming substrate, and an electrically operated vapouriser, are known. A cartridge comprising both a supply of aerosol-forming substrate and a vapouriser is sometimes referred to as a "cartomiser". The vapouriser is typically a heater assembly. In some known examples, the aerosol-forming substrate is a liquid aerosol-forming substrate and the vapouriser comprises a coil of heater wire wound around an elongate wick soaked in liquid aerosol-forming substrate. The cartridge portion typically comprises not only the supply of aerosol-forming substrate and an electrically operated heater assembly, but also a mouthpiece, which the user sucks on in use to draw aerosol into their mouth. Thus, electrically operated smoking systems that vaporize an aerosol-forming liquid by heating to form an aerosol typically comprise a coil of wire that is wrapped around a capillary material that holds the liquid. Electric current passing through the wire causes resistive heating of the wire which vaporises the liquid in the capillary material. The capillary material is typically held within an airflow path so that air is drawn past the wick and entrains the vapour. The vapour subsequently cools to form an aerosol.

This type of system can be effective at producing aerosol but it can also be challenging to manufacture in a low cost and repeatable way. Furthermore, the wick and coil assembly, together with associated electrical connections, can be fragile and difficult to handle.

Other known systems comprise a mesh heater arranged on or proximate to a capillary material arranged to convey aerosol-forming liquid from a liquid storage portion to the mesh heater. In use, electric current is passed through the mesh to cause resistive heating which vaporises the liquid in the capillary material. However, with such systems, heat from the mesh may also be transferred to the aerosol-forming liquid held in the liquid storage portion. This may result in energy losses which reduce the efficiency of the aerosol-generating system. It may also adversely affect the properties of the aerosol-forming liquid held in the liquid storage portion.

According to a first aspect of the present invention, there is provided a heater assembly for use in an aerosol-generating system having a liquid storage portion for holding a liquid aerosol-forming substrate, the heater assembly comprising: an electric heater for heating the liquid aerosol-forming substrate to form an aerosol; and a capillary body for conveying the liquid aerosol-forming substrate from the liquid storage portion of the aerosol-generating system to the electric heater, wherein the electric heater is arranged on an outer surface of the capillary body and comprises a heating layer comprising a porous sheet of electrically conductive material, and wherein the porous sheet is shaped to define a plurality of recesses on its lower surface for retaining the liquid aerosol-forming substrate by capillary action, and wherein at least part of each of the plurality of recesses is spaced from the outer surface of the capillary body in a perpendicular direction.

With the claimed arrangement, aerosol-forming liquid from the capillary material is drawn onto the porous sheet by capillary action and is retained in the plurality of recesses on the lower surface of the porous sheet. As the recesses are spaced from the capillary body, when the electric heater is operated, heat from the heating layer is concentrated on the liquid aerosol-forming substrate retained in the recesses. This may reduce the amount of heat transferred from the heater to liquid stored in the capillary body and in the liquid storage portion, reducing power consumption and facilitating more efficient operation than heater assemblies in which the liquid is vaporised while absorbed in the capillary body. It may also increase the surface area of the heating layer which is in contact with aerosol-forming liquid relative to an entirely flat heater further reducing power consumption for a given amount of aerosol generated, leading to more efficient operation.

As used herein, the term "porous sheet" refers to a layer of material which is formed from a material that is fluid permeable and allows aerosol to pass through it. The term "porous" is intended to encompass materials that are inherently porous as well as substantially non-porous materials that are made porous or permeable through the provision of a plurality of apertures.

As used herein, the term "shaped" is used to mean that the sheet is deformed without removal of material from the sheet.

As used herein, the term "recess" refers to a portion of the lower surface which is set back from the rest of the lower surface. This is distinct from a simple aperture through a flat sheet, such as the apertures in a mesh. The plurality of recesses may each have a depth of from about 20 microns to about 1000 microns. The plurality of recesses may each have a width of from about 20 microns to about 2000 microns.

As used herein, the terms "upper surface" and "lower surface" refer to opposed faces of the porous sheet on either side of the plane of the sheet. The upper surface refers to the face of the sheet which is furthest from the capillary body. The lower surface refers to the face of the sheet which is opposite to the upper surface and is the face closest to the capillary body.

The plurality of recesses may be formed in the porous sheet in any suitable way. Preferably, the porous sheet is embossed and further comprises a plurality of raised portions on its upper surface, the plurality of recesses being defined by the plurality of raised portions. Such embossing may be a simple and cost effective means of providing the plurality of recesses. Such embossing may allow the thickness of the porous sheet to remain substantially constant for more consistent heating.

As used herein, the term "embossed" is used to mean that the sheet is moulded or stamped such that it has one or more features on its upper surface which are raised from the upper surface in slight relief. Preferably, the sheet thickness remains substantially constant. The sheet thickness is distinct from the sheet height, which refers to the difference between the lowest point on the lower surface to the highest point on the upper surface. The sheet thickness at any given point on the sheet should be measured in a direction perpendicular to the lower surface of the sheet at said given point.

The embossing may take any suitable form. For example, the embossing may comprise one or both of a uniform distribution and a non-uniform distribution.

Preferably, the porous sheet is corrugated. Having a porous corrugated sheet may be a particularly simple and cost effective means of providing the plurality of recesses in the sheet.

As used herein, the term "corrugated" refers to a sheet which is shaped into a series of parallel ridges and grooves. In this manner, the corrugation ridges form both the plurality of raised portions on the upper surface of the sheet and the plurality of recesses on the lower surface of the sheet. The corrugation troughs are formed in the region of the sheet between adjacent raised portions (as viewed from the upper surface of the sheet) and between adjacent recesses (as viewed from the lower surface of the sheet).

Preferably, the porous sheet comprises a plurality of apertures. Preferably, the plurality of apertures comprises a first set of apertures located in a first region of the porous sheet, and a second set of apertures located in a second region of the porous sheet, wherein the mean size of the first set of apertures differs from the mean size of the second set of apertures. The size of the apertures in the first and second regions, or the relative position of the first and second regions can be selected based on the air flow characteristics of the aerosol-generating system, or on the temperature profile of the heater assembly, or both. The mean diameter of the first set of apertures may be greater than the mean diameter of the second set of apertures and the first region may be positioned towards the centre of the porous sheet relative to the second region. This may increase the flow rate in a central region of the heater.

Preferably, each aperture has a size of from about 20 square microns to about 10,000 square microns.

Preferably, the plurality of apertures are arranged such that each of the plurality of recesses, when viewed in cross-section, has a single aperture positioned at or proximate to the recess' deepest point. This may help to maximise the liquid retention region defined by each recess. This may also help to facilitate fluid flow through the electric heater when the liquid is retained in the recesses.

Preferably, the porous sheet comprises a capillary porous coating on its lower surface. Preferably the capillary porous coating is provided on at least the portion of the lower surface of the porous sheet which defines the recesses. More preferably, the capillary porous coating is provided over substantially the entire area of the lower surface of the porous sheet. Such a capillary porous coating may help to increase the capillarity of the porous sheet. This may facilitate retention by capillary action of the liquid aerosol-forming substrate against the porous sheet and away from the capillary body.

Suitable capillary porous coatings may include cellulose based coatings, polymer based coatings, foam based coatings, and clay based coatings.

Preferably, the porous sheet is a first porous sheet and the electric heater further comprises a second porous sheet which is positioned parallel to the first porous sheet and between the first porous sheet and the capillary body. By providing a second porous sheet which is positioned parallel to the first porous sheet and between the first porous sheet and the capillary body, heat generated by the first porous sheet can be concentrated on liquid held between the first and second porous sheets. This may help to isolate the heated liquid between the first and second porous sheets from the capillary body, and hence reduce heat dissipation to liquid absorbed in the capillary body. The second porous sheet may have any of the features described above or below in respect of the first porous sheet.

Preferably, the second porous sheet is formed from a thermally insulative material. This may help to further concentrate heat generated by the first porous sheet on the liquid held between the first and second porous sheets, while the capillary body is insulated from the first porous sheet by the second porous sheet. This may further reduce the power required to vaporise the aerosol-forming liquid, and hence reduce the heat dissipation to liquid absorbed in the capillary body.

In some embodiments, the second porous sheet may be a porous sheet of electrically conductive material and form a further heating layer of the electric heater.

Preferably, the first and second porous sheets each comprise a plurality of apertures. In such embodiments, preferably the plurality of apertures of the first porous sheet are transversely offset from the plurality of apertures of the second porous sheet, and the first and second porous sheets are moveable relative to each other from a closed position, in which the plurality of apertures of one or both of the first and second porous sheets are closed by a solid region of the other of the first and second porous sheets, to an open position, in which at least a portion of the first porous sheet and the second porous sheet are separated by a spacing. With this arrangement, the fluid flow through the electric heater may be reduced or prevented when the first and second porous sheets are in the closed position to reduce or prevent leakage of liquid aerosol-forming substrate from the capillary body when the heater assembly is not in use, while allowing normal fluid flow when the porous sheets are in the open position. Preferably, the first and second porous sheets are configured to move into the open position when a current is supplied to the electric heater.

Preferably, the first porous sheet and the second porous sheet are formed from different materials having different thermal expansion coefficients so that one or both of the first and second porous sheets automatically deforms from the closed position to the open position upon heating. That is, the porous sheet is preferably arranged to deform between the closed position and the open position when undergoing a change from a first temperature to a second temperature. The change in temperature can be induced by passing an electric current through one or both of the porous sheets. By forming the first porous sheet and the second porous sheet from different materials having different thermal expansion coefficients so that one or both of the first and second porous sheets automatically deforms from the closed position to the open position upon heating, a simple means for reducing or preventing fluid leakage before use is provided. For example, when the electric heater is in an off state, the porous sheets may be at an ambient temperature. At this ambient temperature the sheets are arranged in the closed position, and hence fluid leakage can be prevented. However, when an electric current is passed through one or both of the first and second porous sheets, the temperature of one or both of the first and second porous sheets increases. Such a temperature change can cause one or both of the sheets to deform from the closed position to the open position and thereby allow normal fluid flow.

Preferably, the heater assembly further comprises an actuator for selectively moving one or both of the first and second porous sheets between the closed and open positions. By providing the heater assembly with an actuator for selectively moving one or both of the first and second porous sheets between the closed and open positions, fine control of the relative position of the first and second porous sheets may be provided. The actuator may also allow the first or second porous sheet to be moved between the open and closed positions with little or no time delay.

Preferably, the spacing between the first and second porous sheets in the closed position is selectively adjustable. With this arrangement, the volume defined between the first and second porous sheets may be selectively adjusted according to user requirements. For example, one or more of desired aerosol-forming liquid consumption rate, rate of puffs, and the temperature rating of the electric heater may be selectively adjusted according to user requirements.

Preferably, the electric heater further comprises a third porous sheet which is positioned parallel to and between the first and second porous sheets. The third porous sheet may have any of the features described above or below in respect of one or both of the first and second porous sheets. For example, the first, second and third porous sheets may each comprise a plurality of apertures.

The plurality of apertures of the second porous sheet may be substantially aligned with the plurality of apertures of the third porous sheet. This may facilitate fluid flow through the electric heater.

Preferably, the second and third porous sheets each comprise a plurality of apertures, wherein the plurality of apertures of the second porous sheet are transversely offset from the plurality of apertures of the third porous sheet. In such embodiments, preferably the third porous sheet is moveable from a closed position, in which the plurality of apertures of the second porous sheet are closed by a solid region of the third porous sheet, to an open position in which at least a portion of the second and third porous sheets are spaced apart. With this arrangement, the first porous sheet may be moved towards the third porous sheet during use to progressively heat liquid retained between the first and third porous sheets. This may improve the efficiency of heating. In certain examples, the first porous sheet is moveable between the first and second positions when the third porous sheet is in the closed position. This may allow the first porous sheet to heat a predetermined amount of liquid trapped between the first and third porous sheets. As well as improving the efficiency of heating, this may facilitate more consistent aerosol properties from puff to puff.

The first and second porous sheets may be fixed in position relative to each other and to the capillary body. Preferably, when the third porous sheet is in the closed position, the first porous sheet is moveable in a perpendicular direction from a first position in which at least a portion of the first and third porous sheets are separated by a first spacing, to a second position in which the first and third porous sheets are separated by a second spacing which is less than the first spacing.

As used herein, the term "capillary body" refers to a component of the heater assembly that is able to convey the liquid aerosol-forming substrate to the electric heater by capillary action. The capillary body may be made of a capillary material. A capillary material is a material that actively conveys liquid from one end of the material to another. The capillary material may have a fibrous or spongy structure. The capillary material preferably comprises a bundle of capillaries. For example, the capillary material may comprise a plurality of fibres or threads or other fine bore tubes. The fibres or threads may be generally aligned to convey liquid aerosol-forming substrate towards the aerosol-generating element. Alternatively, the capillary material may comprise sponge-like or foam-like material. The structure of the capillary material forms a plurality of small bores or tubes, through which the liquid aerosol-forming substrate can be transported by capillary action. The capillary material may comprise any suitable material or combination of materials. Examples of suitable materials are a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres or ceramic. The capillary material may have any suitable capillarity and porosity so as to be used with different liquid physical properties. The liquid aerosol-forming substrate has physical properties, including but not limited to viscosity, surface tension, density, thermal conductivity, boiling point and vapour pressure, which allow the liquid aerosol-forming substrate to be transported through the capillary medium by capillary action.

According to a second aspect of the present invention there is provided a cartridge for use in an aerosol-generating system, the cartridge comprising a liquid storage portion for holding a liquid aerosol-forming substrate; and a heater assembly according to the first aspect of the present invention.

The cartridge may comprise a housing having a connection end and a mouth end remote from the connection end, the connection end configured to connect to a control body of an aerosol-generating system. The housing may define the liquid storage portion. Electrical power may be delivered to the heater assembly from a connected control body through the connection end of the housing. The cartridge may have an air inlet. The mouth end may have a mouth end opening in fluid communication with the air inlet. The cartridge may have an airflow path extending between the air inlet and the mouth end opening.

The housing may be elongate. The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. The material may be light and non-brittle. The housing may comprise any of the features of the housing described in relation to the first aspect of the invention.

The cartridge may comprise a removable mouthpiece through which aerosol may be drawn by a user. The removable mouthpiece may cover the mouth end opening. Alternatively the cartridge may be configured to allow a user to draw directly on the mouth end opening.

The liquid storage portion of the cartridge may be refillable with liquid aerosol-forming substrate. Alternatively, the cartridge may be designed to be disposed of when the storage compartment becomes empty of liquid aerosol-forming substrate.

According to a third aspect of the present invention there is provided an aerosol-generating system comprising: an aerosol-generating device; and a cartridge according to the second aspect of the present invention, wherein the cartridge is removably coupled to the aerosol-generating device, and wherein the aerosol-generating device includes a power supply for the heater assembly.

The device may comprise control circuitry configured to control a supply of power from the power supply to the aerosol-generating element. The control circuitry may comprise a microcontroller. The microcontroller is preferably a programmable microcontroller. The control circuitry may comprise further electronic components. The control circuitry may be configured to regulate a supply of power to the aerosol-generating element. Power may be supplied to the aerosol-generating element continuously following activation of the system or may be supplied intermittently, such as on a puff-by-puff basis. The power may be supplied to the aerosol-generating element in the form of pulses of electrical current.

The aerosol-generating element may comprise an independent power supply. The aerosol-generating system may comprise a first power supply arranged to supply power to the control circuitry and a second power supply configured to supply power to the aerosol-generating element.

The power supply may be a DC power supply. The power supply may be a battery. The battery may be a Lithium based battery, for example a Lithium-Cobalt, a Lithium-Iron-Phosphate, a Lithium Titanate or a Lithium-Polymer battery. The battery may be a Nickel-metal hydride battery or a Nickel cadmium battery. The power supply may be another form of charge storage device such as a capacitor. The power supply may require recharging and be configured for many cycles of charge and discharge. The power supply may have a capacity that allows for the storage of enough energy for one or more user experiences; for example, the power supply may have sufficient capacity to allow for the continuous generation of aerosol for a period of around six minutes, corresponding to the typical time taken to smoke a conventional cigarette, or for a period that is a multiple of six minutes. In another example, the power supply may have sufficient capacity to allow for a predetermined number of puffs or discrete activations of the atomising assembly.

The aerosol-generating system may be a handheld aerosol-generating system configured to allow a user to suck on a mouthpiece to draw an aerosol through the mouth end opening. The aerosol-generating system may have a size comparable to a conventional cigar or cigarette. The aerosol-generating system may have a total length between about 30 mm and about 150 mm. The aerosol-generating system may have an external diameter between about 5 mm and about 30 mm.

Although the system of the invention has been described as comprising a cartridge and a control body, it is possible to implement the invention in a one-piece system.

The cartridge or aerosol-generating system in any of the aspects of the invention may comprise a puff detector in communication with the control circuitry. The puff detector may be configured to detect when a user draws through the airflow passage.

The cartridge or aerosol-generating system in any of the aspects of the invention may comprise a temperature sensor in communication with the control circuitry. The cartridge, control body or aerosol-generating system may comprise a user input, such as a switch or button. The user input may enable a user to turn the system on and off.

The cartridge or aerosol-generating system may also comprise indication means for indicating the determined amount of liquid aerosol-forming substrate held in the liquid storage portion to a user. The control circuitry may be configured to activate the indication means after a determination of the amount of liquid aerosol-forming substrate held in the liquid storage portion has been made.

The indication means may comprise one or more of lights, such as light emitting diodes (LEDs), a display, such as an LCD display and audible indication means, such as a loudspeaker or buzzer and vibrating means. The control circuitry may be configured to light one or more of the lights, display an amount on the display, emit sounds via the loudspeaker or buzzer and vibrate the vibrating means.

Features of one aspect of the invention may be applied to the other aspects of the invention.

As used herein, the term "capillary body" refers to a component of the heater assembly that is able to convey the liquid aerosol-forming substrate to the electric heater by capillary action.

As used herein, the term "electrically conductive material" denotes a material having a resistivity of $1 \times 10^{-2}$ $\Omega$m, or less.

As used herein, the terms "thermally insulating material" and "thermally insulative material" refer to a material having a thermal conductivity of less than 100 W/m·K, preferably less than 40 W/m·K, or less than 10 W/m·K, at 23 degrees Celsius and a relative humidity of 50 percent.

As used herein, the term 'aerosol former' is used to describe any suitable known compound or mixture of compounds that, in use, facilitates formation of an aerosol.

As used herein, the term "liquid aerosol-forming substrate" refers to an aerosol-forming substrate that is in a liquid rather than a solid form. A liquid aerosol-forming substrate may be at least partially absorbed by a liquid retention medium. A liquid-aerosol-forming substrate includes an aerosol-forming substrate in the form of a gel.

As used herein, the term "liquid retention medium" refers to a component that is capable of releasably retaining a liquid aerosol-forming substrate. The liquid retention medium may be, or may comprise, a porous or fibrous material that absorbs or otherwise retains a liquid aerosol-forming substrate that it is brought into contact with while allowing the liquid aerosol-forming substrate to be released by vaporisation.

As used herein, the terms 'upstream' and 'downstream' are used to describe the relative positions of elements, or portions of elements, of the heater assembly, cartridge, or aerosol-generating system in relation to the direction in which air is drawn through the system during use thereof.

As used herein, the term 'longitudinal' is used to describe the direction between the upstream end and the downstream end of the heater assembly, cartridge, or aerosol-generating system and the term 'transverse' is used to describe the direction perpendicular to the longitudinal direction. With reference to the heater assembly, the term 'transverse' refers to the direction parallel to the plane of the porous sheet or sheets, while the term 'perpendicular' refers to the direction perpendicular to the plane of the porous sheet or sheets.

As used herein, the term 'diameter' is used to describe the maximum dimension of the heater assembly, the cartridge, or the system, or a component thereof, in the transverse direction of the heater assembly, the cartridge, or the system. As used herein, the term 'length' is used to describe the maximum dimension in the longitudinal direction.

As used herein, the term 'removably coupled' is used to mean that two or more components of the system, such as the cartridge and the aerosol-generating device can be coupled and uncoupled from one another without significantly damaging either component.

As used herein, "substantially flat" preferably means formed in a single plane and for example not wrapped around or other conformed to fit a curved or other non-planar shape. A flat electric heater can be easily handled during manufacture and provides for a robust construction.

Embodiments of the invention will now be described in detail, by way of example only, with reference to the accompanying drawings, in which.

Figure 1:
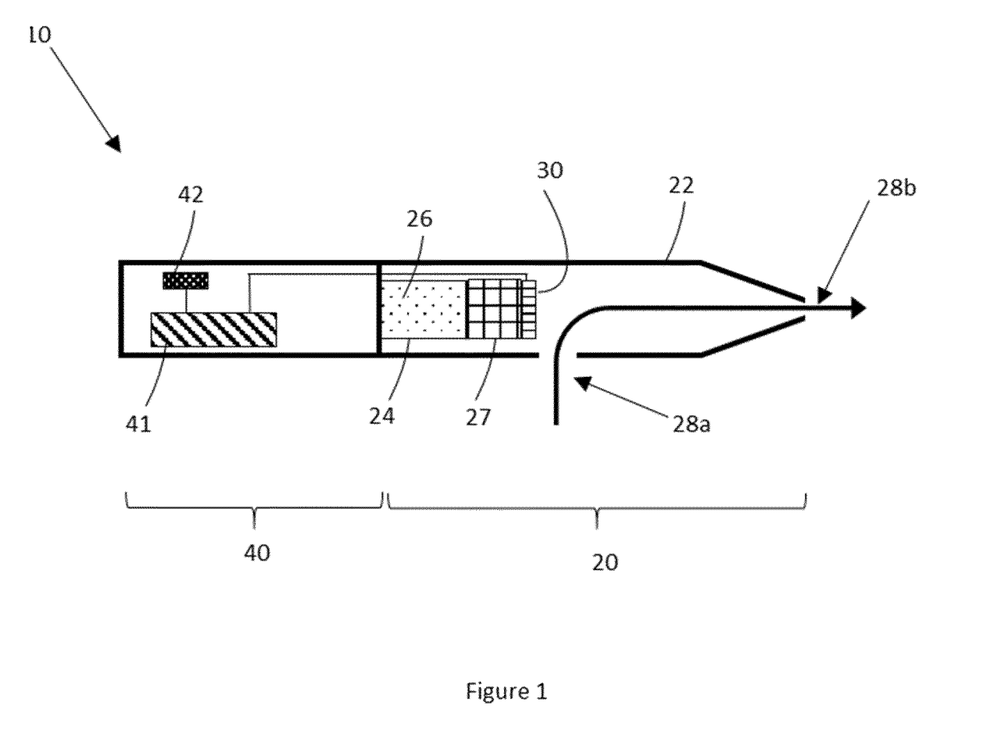
FIG. 1 shows a schematic view of an aerosol-generating system according to a first embodiment of the present invention.

FIG. 1 is a schematic view of an aerosol-generating system 10 comprising a cartridge 20, and an aerosol-generating device 40 that are coupled together. The device comprises a power supply 41, in the form of a battery, and control circuitry 42 coupled to the power supply 41.

The cartridge assembly 20 comprises a housing 22, which forms a mouthpiece for the system. Within the housing there is a storage container 24 holding liquid aerosol-forming substrate 26. A capillary body 27 is disposed adjacent to an open end of the liquid storage container 24. An electric heater 30 is provided adjacent to an outer surface of the capillary body 27, so that the capillary body 27 can convey the liquid aerosol-forming substrate 26 from the liquid storage container 26 to the electric heater 30. The capillary body 27 and the electric heater 30 together form at least part of a heater assembly 31.

The electric heater 30 is also disposed adjacent to an airflow path in the cartridge 20. The airflow path is indicated by a curved arrow in FIG. 1. The airflow path extends from an air inlet 28a to a mouth end opening 28b in the cartridge housing 22.

When the cartridge 20 is coupled to the aerosol-generating device 40 as shown in FIG. 1, the electric heater 30 is electrically coupled to the power supply 41. The device 40 therefore functions to supply electrical power to the electric heater 30 in the cartridge 20 in order to vaporise the liquid aerosol-forming substrate. The vaporised aerosol-forming substrate is entrained in an airflow through the system, the airflow resulting from a user puffing on a mouth end of the cartridge 20. The vaporised aerosol-forming substrate cools in the airflow to form an aerosol before being drawn into a user's mouth.

Figure 2:
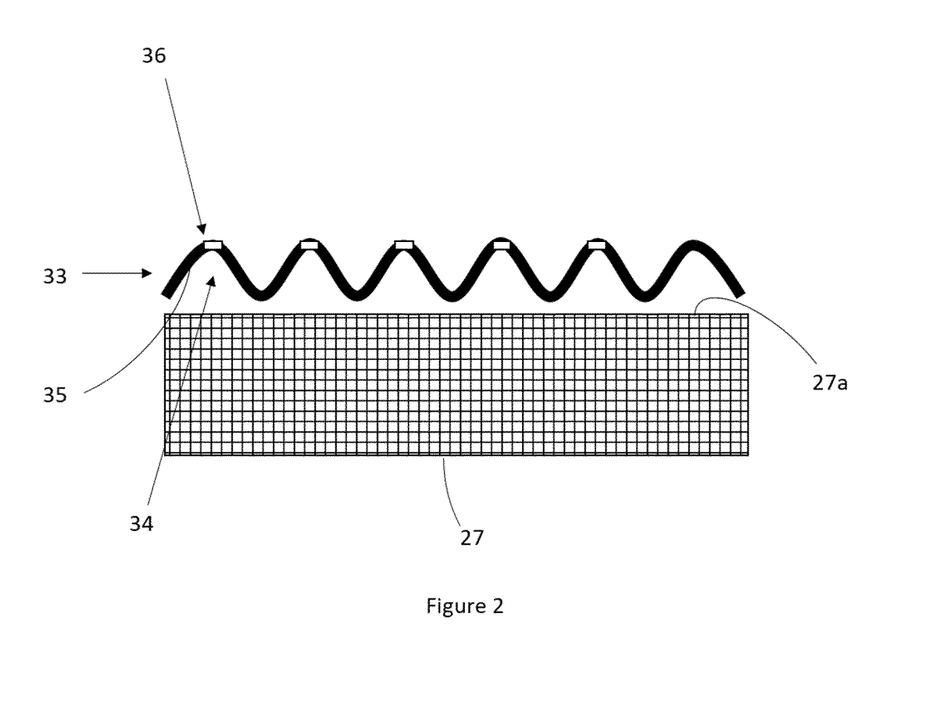
FIG. 2 shows an enlarged view of a portion of the cartridge shown in FIG. 1.

FIG. 2 shows an enlarged view of a portion of the cartridge shown in FIG. 1. This portion forms at least part of the heater assembly 31. As shown in FIG. 2, the electric heater comprises a porous sheet 33 of electrically conductive material. The sheet 33 is shaped to define a plurality of recesses 34 on its lower surface 35. The recesses 34 are arranged to retain the liquid aerosol-forming substrate by capillary action. As shown in FIG. 2, at least part of each of the plurality of recesses 34 is spaced from the outer surface 27a of the capillary body 27 in a perpendicular direction. In the embodiment of FIG. 2, the porous sheet 33 is corrugated to define the plurality of recesses 34. Although not visible in FIG. 32, the lower surface 35 of the porous sheet 33 is provided with a capillary coating.

The porous sheet 33 is provided with a plurality of apertures 36, with a single aperture being positioned at a corresponding recess' deepest point. The apertures 36 are sized to allow liquid aerosol-forming substrate to pass from the lower surface 35 of the porous sheet 33 to the outer surface 37 of the porous sheet 33.

Figure 3A:
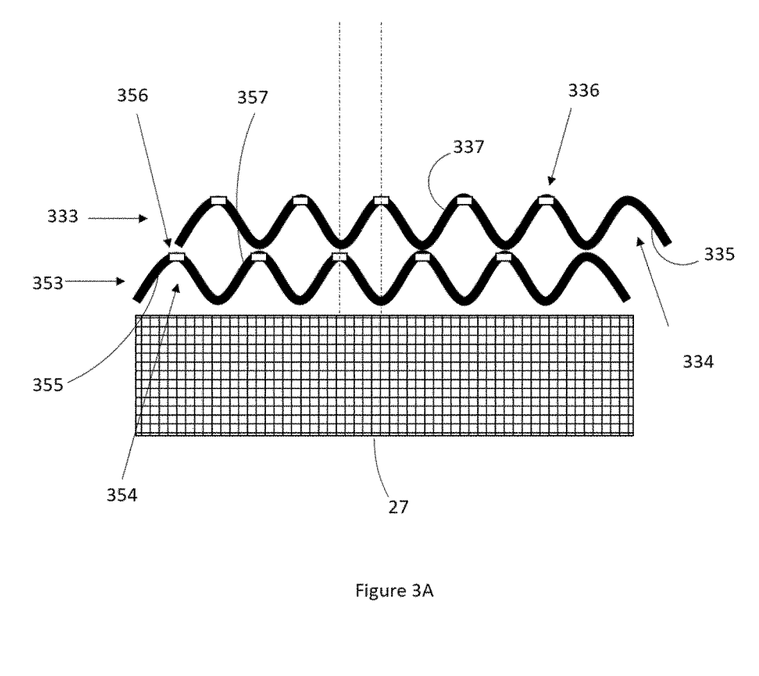
FIG. 3A shows a heater assembly according to a second embodiment of the present invention, in a closed condition.

FIG. 3A shows a heater assembly 331 according to a second embodiment of the present invention. The heater assembly 331 comprises a first porous sheet 333, which corresponds to the porous sheet 33 of the embodiment of FIG. 2. That is, the first porous sheet 333 is shaped to define a plurality of recesses 334 on its lower surface 335. The recesses 334 are arranged to retain the liquid aerosol-forming substrate by capillary action. The first porous sheet 333 is provided with a plurality of apertures 336, with a single aperture being positioned at a corresponding recess' deepest point. The apertures 336 are sized to allow liquid aerosol-forming substrate to pass from the lower surface 335 of the first porous sheet 333 to the upper surface 337 of the first porous sheet 333.

The heater assembly 331 also comprises a second porous sheet 353 positioned between the first porous sheet 333 and the capillary body 27. The second porous sheet 353 is shaped to define a plurality of recesses 354 on its lower surface 355. The recesses 354 are arranged to retain the liquid aerosol-forming substrate by capillary action. The second porous sheet 353 is provided with a plurality of apertures 356, with a single aperture being positioned at a corresponding recess' deepest point. The apertures 356 are sized to allow liquid aerosol-forming substrate to pass from the lower surface 355 of the second porous sheet 353 to the outer surface 357 of the second porous sheet 353.

The first and second porous sheets 333, 353 are arranged such that the plurality of apertures 336 of the first porous sheet 333 are transversely offset from the plurality of apertures 356 of the second porous sheet 353. The first and second porous sheets 333, 353 are also moveable relative to each other from a closed position in which the plurality of apertures 356 of the second porous sheet 353 are closed by a solid region of the first porous sheet 333, to an open position, in which at least a portion of the first porous sheet 333 and the second porous sheet 353 are separated by a spacing 370. This can be best appreciated with references to both FIGS. 3A and 3B, which respectively show the closed and open positions.

Figure 3B:
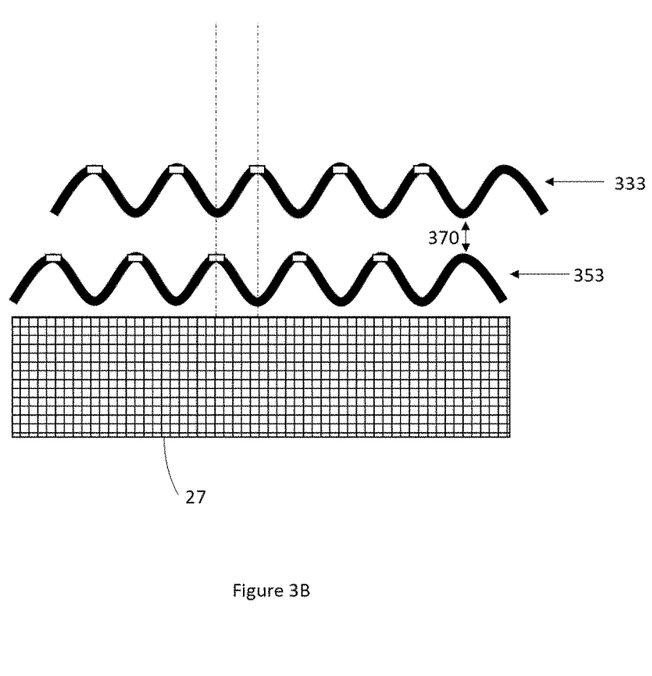
FIG. 3B shows the heater assembly of the second embodiment, in an open position.

In the closed position, liquid can be prevented from passing from the capillary body 27 to the upper surface 337 of the first porous sheet 333, because the apertures 356 of the second porous sheet 353 are closed by a solid region of the first porous sheet 333. However, when the sheets 333, 353 are in the open position, liquid can pass from the capillary body 27, through the apertures 336, 256 of each sheet, and on to the upper surface 337 of the first porous sheet 333.

In the embodiment of FIGS. 3A and 3B, the first porous sheet 333 is electrically connected to the power supply 41 such that it can be used to heat and vaporise liquid aerosol forming substrate. The second porous sheet 333 is formed of a thermally insulative material, since this may help to further concentrate heat generated by the first porous sheet on the liquid held between the first and second porous sheets, while the capillary body is insulated from the first porous sheet by the second porous sheet. This may further reduce the power required to vaporise the aerosol-forming liquid, and hence reduce the heat dissipation to liquid absorbed in the capillary body.

Figure 4A:
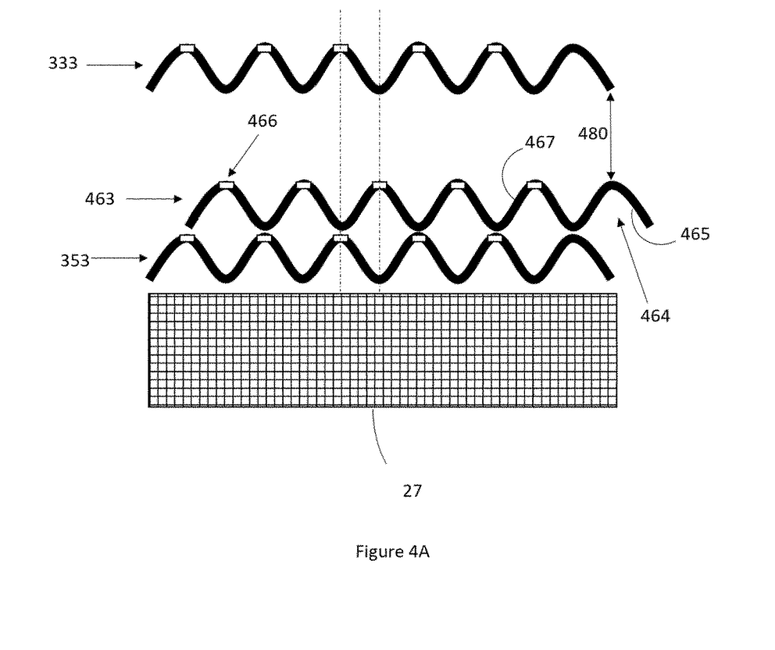
FIG. 4A shows a heater assembly according to a third embodiment of the present invention, in a closed condition.
Figure 4B:
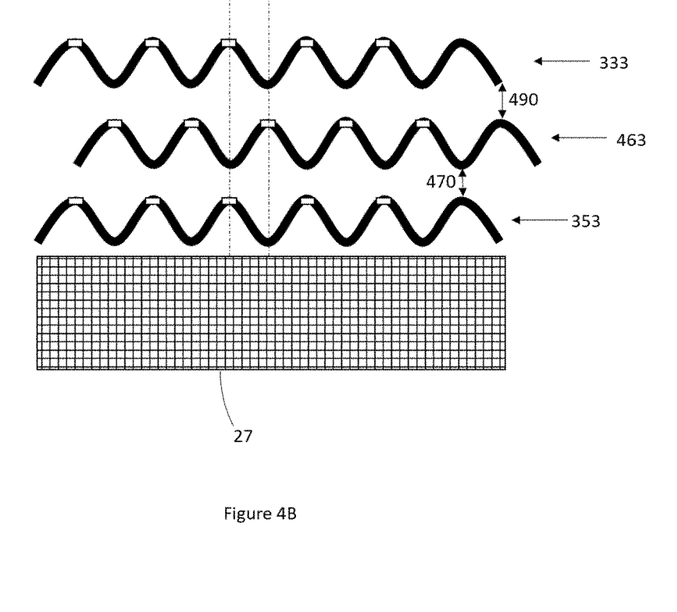
FIG. 4B shows the heater assembly of the third embodiment, in an open position.

FIGS. 4A and 4B shows a heater assembly 431 according to a third embodiment of the present invention. The heater assembly 431 of FIGS. 4A and 4B is similar to the heater assembly 331 of FIGS. 3A and 3B in that it comprises first and second porous sheets 333, 353, which are movable relative to each other. However, the heater assembly 431 of FIGS. 4A and 4B further comprises a third porous sheet 463 which is positioned parallel to and between the first and second porous sheets 333, 353.

The third porous sheet 463 is shaped to define a plurality of recesses 464 on its lower surface 465. The recesses 464 are arranged to retain the liquid aerosol-forming substrate by capillary action. The third porous sheet 463 is provided with a plurality of apertures 466, with a single aperture being positioned at a corresponding recess' deepest point. The apertures 466 are sized to allow liquid aerosol-forming substrate to pass from the lower surface 465 of the third porous sheet 463 to the outer surface 467 of the third porous sheet 463.

The second and third porous sheets 353, 463 are arranged such that the plurality of apertures 356 of the second porous sheet 353 are transversely offset from the plurality of apertures 466 of the third porous sheet 463. The third porous sheet 463 and second porous sheet 353 are also moveable relative to each other between a closed position, in which the plurality of apertures 356 of the second porous sheet 353 are closed by a solid region of the third porous sheet 463, and an open position, in which at least a portion of the second and third porous sheets 353, 463 are spaced apart by a spacing 470. This can be best appreciated with references to both FIGS. 4A and 4B, which respectively show the closed and open positions.

As also illustrated by FIGS. 4A and 4B, the first porous sheet 333 is also movable relative to the third porous sheet 463 in a perpendicular direction between: a first position, in which at least a portion of the first and third porous sheets 333, 463 are separated by a first spacing 480; and a second position, in which the first and third porous sheets 333, 463 are separated by a second spacing 490 which is less than the first spacing 480. This can be best appreciated with references to both FIGS. 4A and 4B, which respectively show the first and second spacings 480, 490.

Although FIGS. 4A and 4B show such movement occurring at the same time as relative movement of the second and third sheets 353, 463 between the open and closed positions, it should be appreciated that the first and third sheets 333, 463 can be moved relative to one another independent of relative movement between the second and third sheets 353, 463. That is, the first porous sheet 333 may be moved relative to the third porous sheet 463, whilst the second and third porous sheets 353, 463 remain in the closed position.

With this arrangement of FIGS. 4A and 4B, the first porous sheet 333 may be moved towards the third porous sheet 463 during use to progressively heat liquid retained between the first and third porous sheets 333, 463. This may improve the efficiency of heating. By arranging for the first porous sheet 333 to be moveable between the first and second positions when the third porous sheet 463 is in the closed position, the first porous sheet 333 can heat a predetermined amount of liquid trapped between the first and third porous sheets 333, 463. As well as improving the efficiency of heating, this may facilitate more consistent aerosol properties from puff to puff.

The invention claimed is:

1. A heater assembly for an aerosol-generating system having a liquid storage portion configured to hold a liquid aerosol-forming substrate, the heater assembly comprising:
    an electric heater configured to heat the liquid aerosol-forming substrate to form an aerosol; and
    a capillary body configured to convey the liquid aerosol-forming substrate from the liquid storage portion of the aerosol-generating system to the electric heater,
    wherein the electric heater is disposed on an outer surface of the capillary body and comprises a heating layer comprising a porous sheet of electrically conductive material, and
    wherein the porous sheet is embossed to define a plurality of recesses on a lower surface thereof configured to retain the liquid aerosol-forming substrate by capillary action and a plurality of corresponding raised portions on an upper surface thereof, the plurality of recesses being defined by the plurality of corresponding raised portions, and
    wherein at least part of each of the plurality of recesses is spaced from the outer surface of the capillary body in a perpendicular direction.

2. The heater assembly according to claim 1, wherein the porous sheet is corrugated.

3. The heater assembly according to claim 1, wherein the porous sheet comprises a plurality of apertures.

4. The heater assembly according to claim 3,
    wherein the plurality of apertures comprises a first set of apertures located in a first region of the porous sheet, and a second set of apertures located in a second region of the porous sheet, and
    wherein the mean size of the first set of apertures differs from the mean size of the second set of apertures.

5. The heater assembly according to claim 3, wherein the plurality of apertures are arranged such that each of the plurality of recesses, when viewed in cross-section, has a single aperture positioned at or proximate to a deepest point of the recesses.

6. The heater assembly according to claim 1, wherein the porous sheet comprises a capillary porous coating on the lower surface of the porous sheet.

7. The heater assembly according to claim 1,
    wherein the porous sheet is a first porous sheet, and
    wherein the electric heater further comprises a second porous sheet, which is disposed parallel to the first porous sheet and between the first porous sheet and the capillary body.

8. The heater assembly according to claim 7,
    wherein the first porous sheet and the second porous sheet each comprise a plurality of apertures,
    wherein the plurality of apertures of the first porous sheet are transversely offset from the plurality of apertures of the second porous sheet, and
    wherein the first porous sheet and the second porous sheet are moveable relative to each other from a closed position, in which the plurality of apertures of one or both of the first and the second porous sheets are closed by a solid region of the other of the first and the second porous sheets, to an open position, in which at least a portion of the first porous sheet and the second porous sheet are separated by a spacing.

9. The heater assembly according to claim 8, wherein the first porous sheet and the second porous sheet are formed from different materials having different thermal expansion coefficients so that one or both of the first and the second porous sheets automatically deforms from the closed position to the open position upon heating.

10. The heater assembly according to claim 8, wherein the heater assembly further comprises an actuator configured to selectively move one or both of the first and the second porous sheets between the closed and the open positions.

11. The heater assembly according to claim 7, wherein the electric heater further comprises a third porous sheet, which is disposed parallel to and between the first and the second porous sheets.

12. The heater assembly according to claim 11,
    wherein the second porous sheet and the third porous sheet each comprise a plurality of apertures,
    wherein the plurality of apertures of the second porous sheet are transversely offset from the plurality of apertures of the third porous sheet, and wherein the third porous sheet is moveable from a closed position, in which the plurality of apertures of the second porous sheet are closed by a solid region of the third porous sheet, to an open position in which at least a portion of the second and the third porous sheets are spaced apart.

13. The heater assembly according to claim 12, wherein, when the third porous sheet is in the closed position, the first porous sheet is moveable in a perpendicular direction from a first position in which at least a portion of the first and the third porous sheets are separated by a first spacing, to a second position in which the first and the third porous sheets are separated by a second spacing, which is less than the first spacing.

14. A cartridge for an aerosol-generating system, the cartridge comprising:
   a liquid storage portion configured to hold a liquid aerosol-forming substrate; and
   a heater assembly according to claim 1.

15. An aerosol-generating system, comprising:
   an aerosol-generating device; and
   a cartridge according to claim 14,
   wherein the cartridge is removably coupled to the aerosol-generating device, and
   wherein the aerosol-generating device includes a power supply for the heater assembly.

\* \* \* \* \*